US009259925B2

(12) United States Patent
Govyadinov et al.

(10) Patent No.: US 9,259,925 B2
(45) Date of Patent: Feb. 16, 2016

(54) DROP DETECTOR

(75) Inventors: Alexander Govyadinov, Corvallis, OR (US); Brett E Dahlgren, Albany, OR (US); Anton Nicholas Clarkson, Corvallis, OR (US); Steven H. Walker, Camas, WA (US); Daniel Burger, Leingarten (DE); Trudy Benjamin, Portland, OR (US)

(73) Assignee: HEWLETT-PACKARD DEVELOPMENT COMPANY, L.P., Houston, TX (US)

( * ) Notice: Subject to any disclaimer, the term of this patent is extended or adjusted under 35 U.S.C. 154(b) by 0 days.

(21) Appl. No.: 14/119,026

(22) PCT Filed: May 27, 2011

(86) PCT No.: PCT/US2011/038322
§ 371 (c)(1),
(2), (4) Date: Nov. 20, 2013

(87) PCT Pub. No.: WO2012/166089
PCT Pub. Date: Dec. 6, 2012

(65) Prior Publication Data
US 2014/0078213 A1   Mar. 20, 2014

(51) Int. Cl.
*B41J 2/165* (2006.01)
*B41J 2/07* (2006.01)
*B41J 2/045* (2006.01)
*B41J 2/155* (2006.01)
(Continued)

(52) U.S. Cl.
CPC *B41J 2/07* (2013.01); *B41J 2/0458* (2013.01); *B41J 2/04561* (2013.01); *B41J 2/155* (2013.01); *B41J 2/165* (2013.01); *B41J 2/2142* (2013.01); *G01N 21/84* (2013.01); *B41J 2202/20* (2013.01)

(58) Field of Classification Search
CPC ............ B41J 2/125; B41J 29/393; B41J 2/01; B41J 2/04561; B41J 2/04508
See application file for complete search history.

(56) References Cited

U.S. PATENT DOCUMENTS 5,742,304 A * 4/1998 Richtsmeier et al. ............ 347/40
7,023,462 B2 * 4/2006 Fukuda ......................... 347/236
7,163,275 B2   1/2007 Yeh et al.
(Continued)

FOREIGN PATENT DOCUMENTS

CN   101148119 A   3/2008
CN   101622134 A   1/2010
(Continued)

OTHER PUBLICATIONS

European Patent Office Munich Germany. European Search Report. Application No. 11866940.7-1701/2714403 PCT/US2011/038322.

*Primary Examiner* — Lamson Nguyen
(74) *Attorney, Agent, or Firm* — Hewlett-Packard Patent Dept (57) ABSTRACT

In one example, a drop detector includes a light source for illuminating drops passing through a drop zone, multiple light detectors near the light source for detecting light scattered off drops passing through the drop zone, and multiple lenses each configured to focus light from the drop zone on one of the light detectors. In one example, each light detector is arranged in the same plane with all of the other light detectors. In one example, the lenses are configured to focus light from two different spaces in the drop zone on different detectors or groups of detectors. In one example, the lenses are configured to focus light from a single space in the drop zone on multiple detectors.

20 Claims, 11 Drawing Sheets (51) Int. Cl.
  *B41J 2/21*     (2006.01)
  *G01N 21/84*    (2006.01)

(56)         References Cited

U.S. PATENT DOCUMENTS 7,815,280  B2   10/2010  Hayashi et al.
  7,862,141  B2    1/2011  Hayashi et al.
  2005/0157161  A1   7/2005  Fukuda
  2009/0058921  A1   3/2009  Habashi 2009/0096826  A1   4/2009  Hayashi
  2009/0244151  A1  10/2009  Hendricks et al.
  2010/0091107  A1   4/2010  Shin et al.
  2010/0177139  A1   7/2010  Na
  2010/0289865  A1* 11/2010  Eyal et al. ..................... 347/246

FOREIGN PATENT DOCUMENTS

JP      2001150696    5/2001
  JP      2007076265    3/2007
  JP      2010167721    8/2010

* cited by examiner

DROP DETECTOR

BACKGROUND

It is sometimes desirable to detect characteristics of ink drops ejected by an inkjet printer. Characteristics of the ink drops may be used to assess the state or "health" of structural and operational features of the printer. For example, detecting that ink drops are absent where they should be present and detecting the number, size and/or shape of ink drops may help determine whether orifices through which ink drops are ejected (or are supposed to be ejected) are partially or fully clogged.

DRAWINGS

The same part numbers designate the same or similar parts throughout the figures.

DESCRIPTION

One of the challenges in the development of light scattering drop detectors (LSDD) for inkjet printers is providing scalability—the efficient adaptation to different printing environments. Examples of the new drop detector were developed in an effort to scale LSDD to page wide array (PWA) inkjet printing environments. Thus, examples will be described with reference to a PWA inkjet printer. Examples of the new drop detector, however, are not limited to PWA inkjet printing but may be used in other printing or drop dispensing environments. The following description, therefore, should not be construed to limit the scope of the invention, which is defined in the claims that follow the description.

In one example of the new drop detector, multiple light detectors are arranged in the same plane with all of the other light detectors and multiple detector lenses are configured to focus light from two different spaces in the drop zone on different detectors or groups of detectors. In another example of the new drop detector, the lenses are configured to focus light from a single space in the drop zone on multiple detectors.

Figure 1:
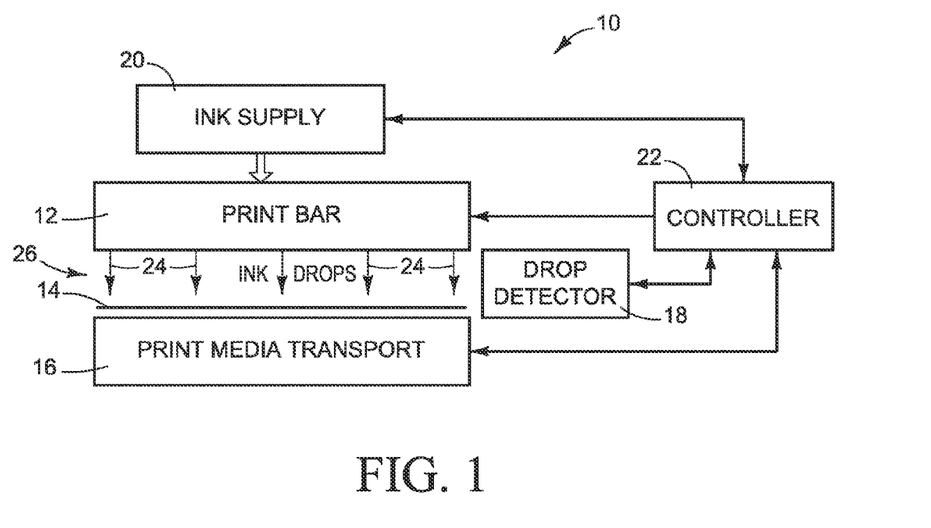
FIG. 1 is a block diagram illustrating one embodiment of an inkjet printer in which examples of the new drop detector may be implemented.

FIG. 1 is a block diagram illustrating one embodiment of an inkjet printer 10 in which examples of the new drop detector may be implemented. Referring to FIG. 1, printer 10 includes a print bar 12 spanning the width of a printable medium 14. Printer 10 also includes a media transport mechanism 16, a drop detector 18, an ink supply 20, and a controller 22. Controller 22 represents generally the programming, processor(s) and associated memories, and the electronic circuitry and components needed to control the operative elements of a printer 10. Print bar 12 represents generally a printhead module or an array of printhead modules carrying one or more printhead dies and the associated mechanical and electrical components for dispensing ink drops on to a sheet or web of paper or other printable medium 14. Print bar 12 may be a single print bar spanning media 14 or multiple print bars that together span media 14. For convenience, print bar 12 is referred to in the singular in the remainder of this Description.

A typical thermal inkjet printhead die, for example, includes an orifice plate arrayed with ink ejection orifices and firing resistors formed on an integrated circuit chip positioned behind the ink ejection orifices. The printhead die(s) in each module are electrically connected to printer controller 22 and fluidically connected to ink supply 20. In operation, printer controller 22 selectively energizes ink ejector elements in a printhead die, or group of printhead dies, in the appropriate sequence to eject ink on to media 14 in a pattern corresponding to the desired printed image. As described in detail below, drop detector 18 includes a light source for illuminating ink drops 24 passing through a drop zone 26 between print bar 12 and media 14 and multiple light detectors for detecting light scattered off drops 24.

Figure 2:
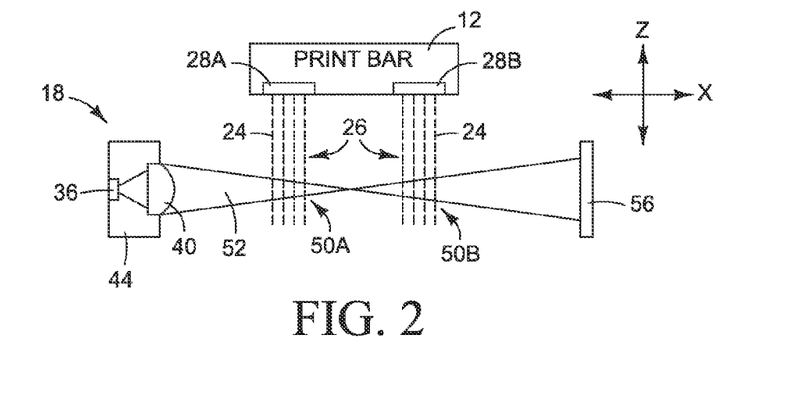
FIGS. 2 and 3 are elevation and bottom plan views, respectively, illustrating a modular drop detector, such as might be used in the printer of FIG. 1, according to one example of the invention.
Figure 3:
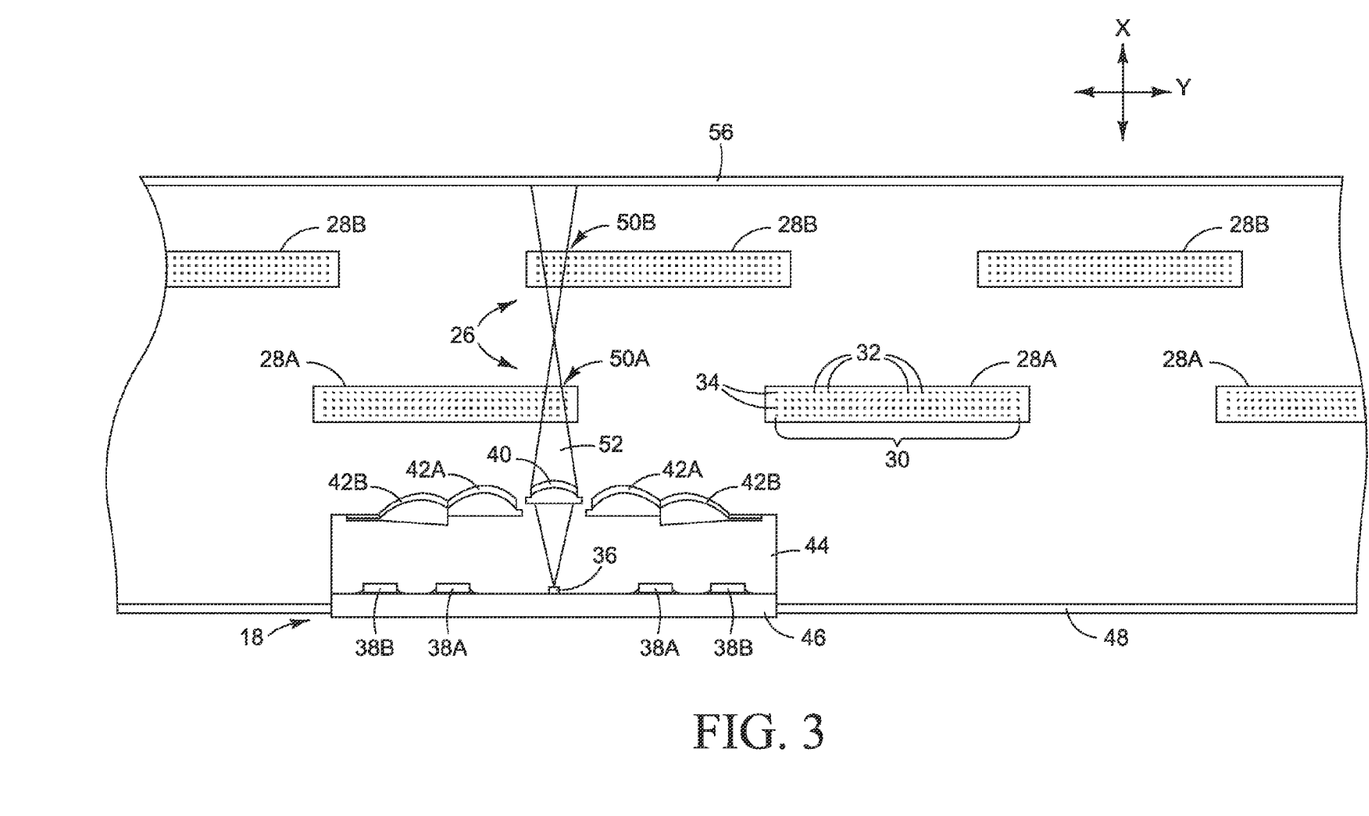

FIGS. 2 and 3 are elevation and bottom plan views, respectively, illustrating one example of a drop detector 18. Referring to FIGS. 2 and 3, print bar 12 includes a media wide array of stationary printhead modules 28A, 28B. Printhead modules 28A, 28B may be arranged, for example, in staggered, overlapping rows as shown in FIG. 3. Each module 28A, 28B includes one or more printhead dies for ejecting ink drops through drop zone 26. Ink drops 24 are ejected from the printhead die(s) on each module 28A, 28B through an array 30 of ink ejection orifices 32. For example, orifice array 30 may include four rows 34 of orifices 32 as shown in FIGS. 2 and 3. The orifices 32 in each row 34, for example, may be used to eject a different color ink.

Drop detector 18 includes a light source 36 for illuminating ink drops 24 and light detectors 38A, 38B for detecting light scattered off illuminated drops 24. In the example shown in FIGS. 2 and 3, drop detector 18 includes a single light source 36 and multiple light detectors 38A and 38B arranged in pairs on opposite sides of light source 36. Drop detector 18 also includes a lens 40 in front of light source 36 and lenses 42A, 42B in front of light detectors 38A, 38B, respectively. As described in more detail below with reference to FIG. 4, lens 40 is configured to focus light from light source 36 on to the desired space or spaces in drop zone 26; lenses 42A are configured to focus light from one space in drop zone 26, for example corresponding to drops ejected by closer printhead modules 28A, on inner light detectors 38A; and lenses 42B are configured to focus light from another space in drop zone 26, for example corresponding to drops ejected by farther printhead modules 28B, on outer light detectors 38B.

In the example shown in FIGS. 2 and 3, light source 36 and light detectors 38A, 38B are housed together as a module 44 mounted on a carriage 46. Carriage 46 moves laterally on a guide rail 48 back and forth along drop zone 26 in a direction transverse to the direction print media 14 moves past print bar 12 (media transport direction) and transverse to the direction drops 24 move through drop zone 26 (drop direction). In some examples for a printer 10 (FIG. 1), these three directions will be substantially orthogonal to one another. Thus, in the example shown in FIGS. 2 and 3, the three directions may be described with reference to the X, Y and Z axes in a Cartesian coordinate system, where media 14 moves in a direction parallel to the X axis, carriage 46 moves in a direction parallel to the Y axis, and drops 24 move in a direction parallel to the Z axis. Other configurations are possible and examples are not limited to orthogonal directions of movement.

Figure 4:
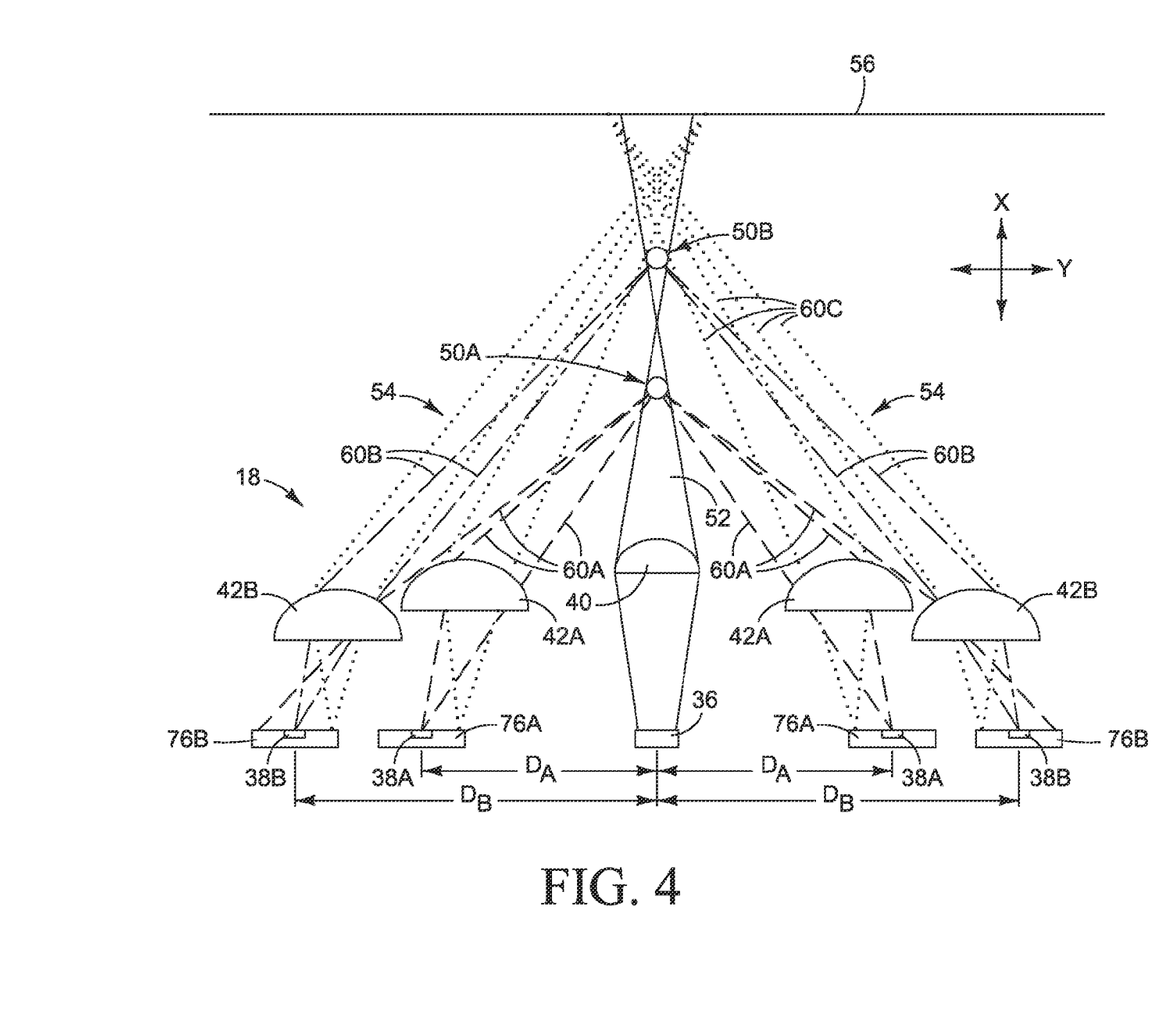
FIG. 4 illustrates a drop detector according to one example of the invention in which multiple detectors are focused on two spaces in the drop zone from both sides of a light source.

FIG. 4 illustrates one example of a drop detector 18 in which light detectors 38A and 38B are focused on two spaces 50A and 50B, respectively, in drop zone 26. Referring now to FIGS. 2-4, light source 36 projects a light beam 52 through drop zone 26 at desired locations along drop zone 26, for example at the direction of controller 22 (FIG. 1). Light 54 scattered off drops 24 is detected by light detectors 38A, 38B which output electrical signals representative of scattered light 54. These signals may be analyzed, for example by controller 22 (FIG. 1), to determine characteristics of drops 24.

Light in beam 52 is scattered off drops 24 in all directions. For clarity in illustrating drop detector 18, however, only light scattered back toward light detectors 38A, 38B is represented by lines 54 in FIG. 4. A backplane 56 positioned opposite drop detector 18 across drop zone 26 may be included to restrict the propagation of light beam 52. Although it may be desirable in some detector applications to use a reflective backplane 52 to help illuminate the drops, it is expected that in most applications for a drop detector 18, a non-reflective backplane 56 will be used to help minimize unwanted scattering of stray light back toward detectors 38A, 38B.

Light source 36 represents generally any source of a light beam suitable for illuminating ink drops 24 including, for example, EELs (edge emitting lasers), VCSELs (vertical cavity surface emitting lasers) and LEDs (light emitting diodes). Light detectors 38A, 38B each represent generally any light detector suitable for detecting light scattered off ink drops 24 including, for example, PIN detectors with integrated transimpedance amplifier, or discrete PIN detectors with external transimpedance amplifier, and phototransistors.

Referring now specifically to FIG. 4, lens 40 is configured to focus light beam 52 on two spaces 50A and 50B in drop zone 26. Closer drop zone detection space 50A, for example, corresponds to the location of printhead modules 28A in FIG. 3 and farther drop zone detection space 50B corresponds to the location of printhead modules 28B in FIG. 3.

Each inner detector lens 42A is configured to focus light reflected from drops passing through closer drop zone space 50A on the corresponding inner light detector 38A, as indicated by dashed lines 60A. Each outer detector lens 42B is configured to focus light from drops passing through farther drop zone space 50B on the corresponding outer light detector 38B, as indicated by phantom lines 60B. Detector lenses 42A, 42B are also configured to direct unwanted light away from detectors 38A, 38B as indicated by dotted lines 60C.

The use of multiple lens/detector pairs 38A/42A, 38B/42B enables the detection of drops passing through two different spaces 50A, 50B in drop zone 26 without refocusing or repositioning any of the components of drop detector 18.

Figure 11:
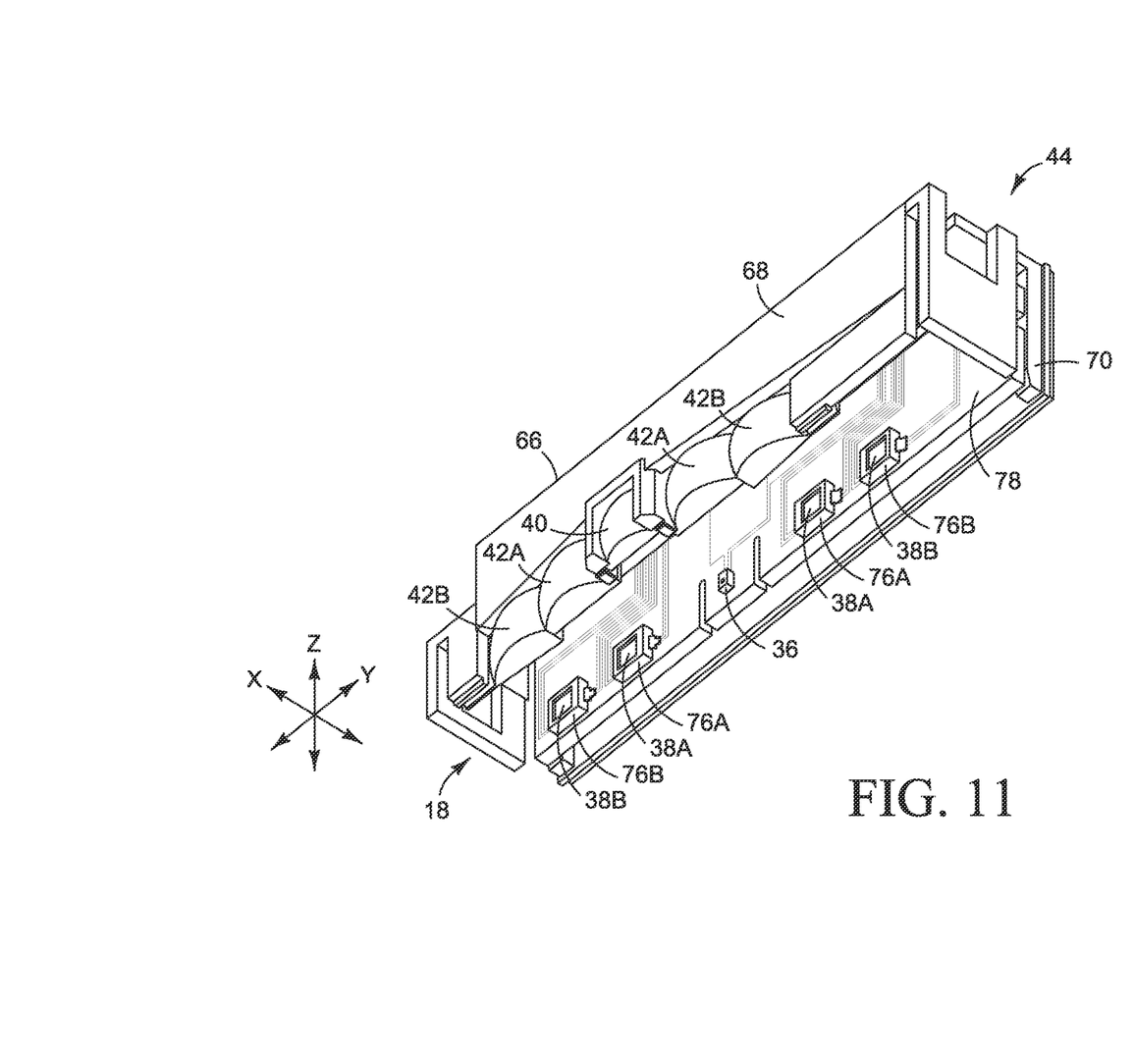
FIG. 11 is a perspective view illustrating part of the interior of the drop detector module of FIGS. 8 and 9 showing one example arrangement of the light detectors.

In the example shown in FIG. 4, two lens/detector pairs 38A/42A, 38B/42B see drops in each drop zone space 50A, 50B, respectively. Each lens/detector pair is positioned opposite the other pair the same distance on each side of light source 36: each inner lens/detector pair 38A/42A is positioned a distance $D_A$ from light source 36; and each outer lens/detector pair 38B/42B is positioned a greater distance $D_B$ from light source 36. The use of multiple light detectors focused on each drop zone space—two detectors 38A, 38B for each space 50A, 50B in this example—increases light collection efficiency from the drop zone, and the corresponding multiple signal channels can be used to improve the signal to noise ratio in the output from drop detector 18. As noted above, each lens 42A, 42B is configured to focus a range of the field (in the X axis in FIG. 4) onto a single detector 38A, 38B. The optical axis of each detector lens 42A, 42B is not parallel to the optical axis of light lens 40, and the curvature of each lens is controlled to help reduce lossy high angle surfaces to capture more light. Also, the flat side of each detector lens 42A, 42B may be wedge shaped as shown in FIGS. 3 and 11 to bend light onto the detectors to help reduce distances $D_A$ and $D_B$ (and thus reduce the size of the detector module) and to help reduce the lossy high angle surfaces to capture more light.

Figure 5:
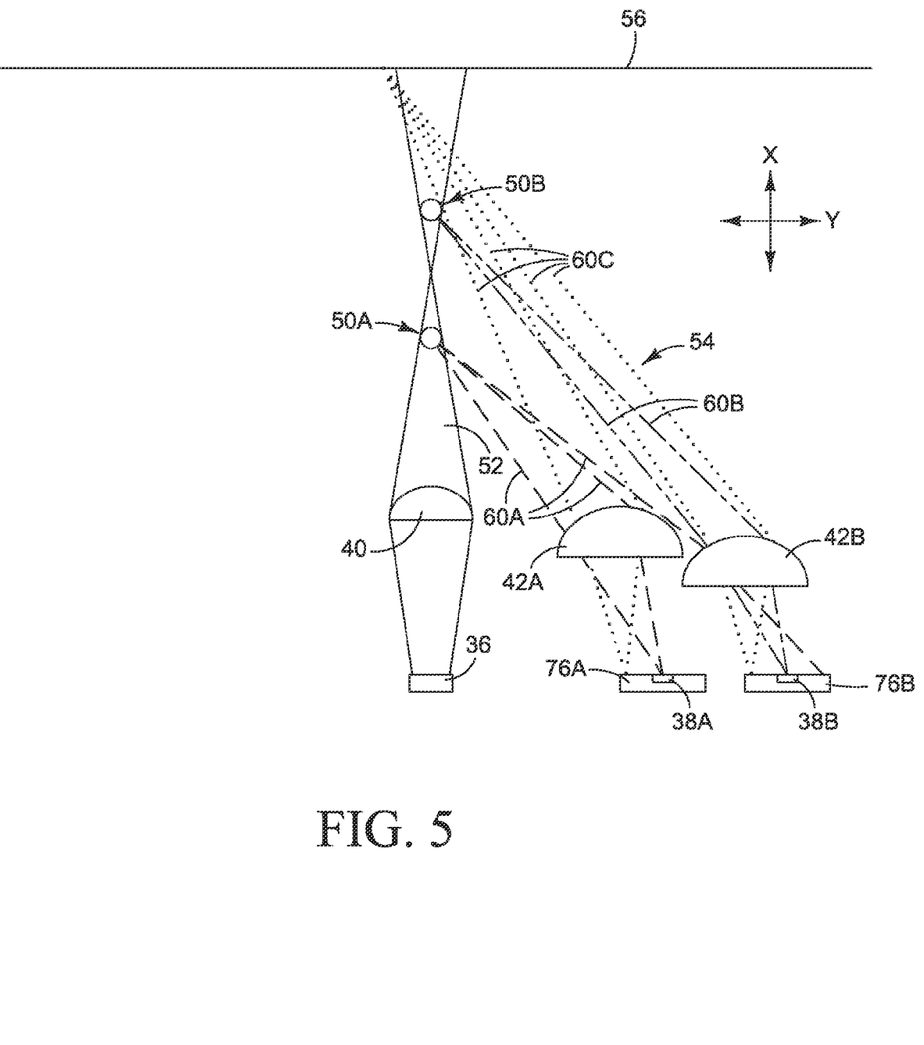
FIG. 5 illustrates a drop detector according to one example of the invention in which multiple lens/detector pairs focus on two spaces in the drop zone from only one side of the light source.

Other suitable detector configurations are possible. More or fewer detectors could be used for each drop zone space, and the number or position of each detector or group of detectors could be different from that shown in FIG. 4. For example, it may be desirable in some applications for a drop detector 18 to include multiple lens/detector pairs but only on one side of the light source, as shown in FIG. 5. For another example, it may be desirable in some applications for a drop detector 18 to include more than two lens/detector pairs focusing on each "target" space in the drop zone. Although a single light source 36 is shown, the use of multiple light sources is possible. Although each lens is 40, 42A and 42B is depicted as a single lens, multiple lenses might be used in some applications or environments to achieve the desired function.

With continued reference to FIG. 4, each light detector 38A, 38B is located in the same plane as all of the other light detectors 38A, 38B. This planar configuration enables a compact modular design suitable for implementation as a scanning drop detector 18 within the architecture of a typical PWA inkjet printer. This planar configuration also facilitates the easy assembly of light detectors 38A, 38B to the underlying printed circuit board (PCB) using conventional automated pick and place tooling.

Figure 6:
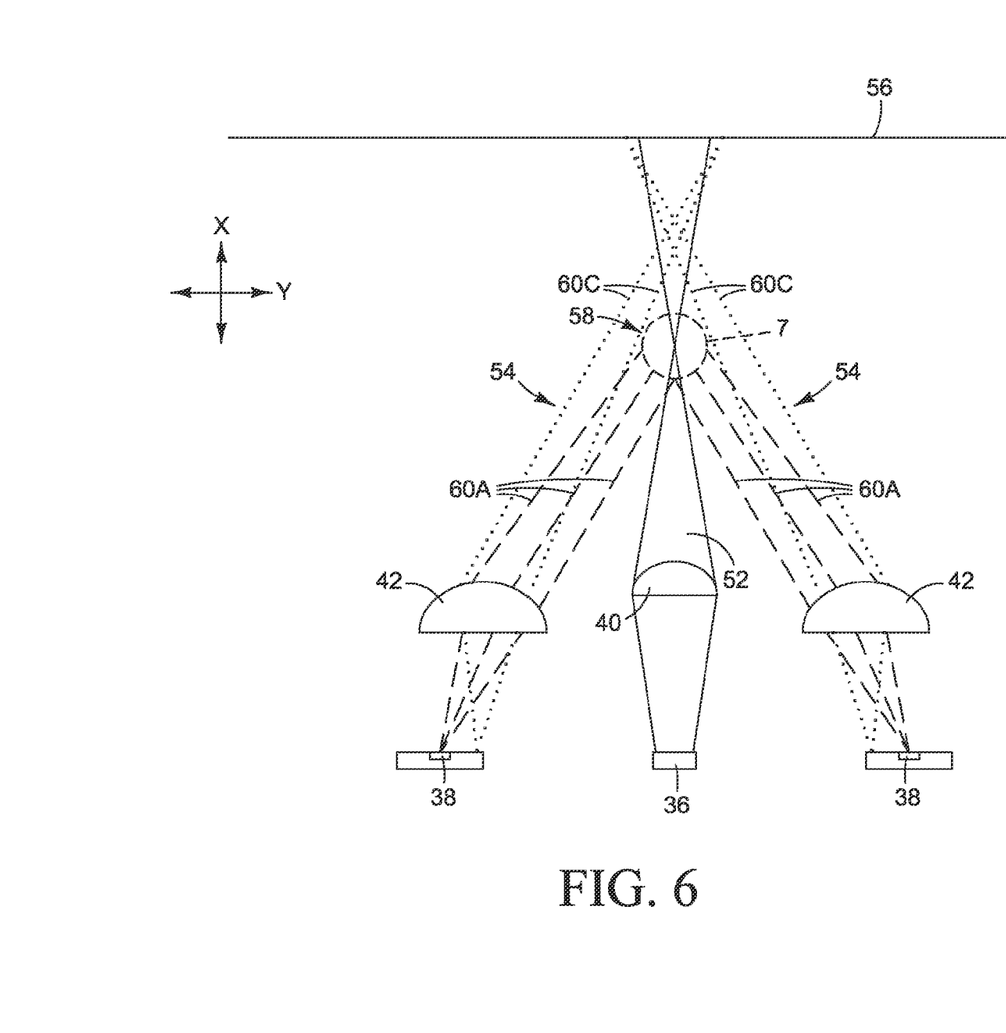
FIG. 6 illustrates a drop detector according to one example of the invention in which multiple detectors are focused on one space in the drop zone.
Figure 7:
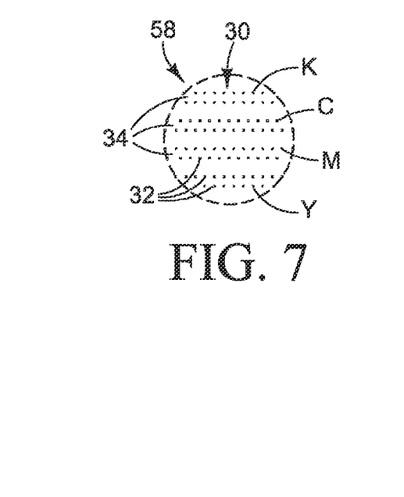
FIG. 7 is a detail view taken from FIG. 5 illustrating the space in the drop zone on which the detectors are focused.

In another example of a drop detector 18 shown in FIG. 6, each of the multiple detectors 38 is focused on the same detection space 58 in drop zone 26. As shown in the detail view of FIG. 7, for example, drop zone space 58 may correspond to an orifice array 30 for ejecting CMYK color ink drops along a single slot, non-staggered PWA printhead architecture.

Figure 8:
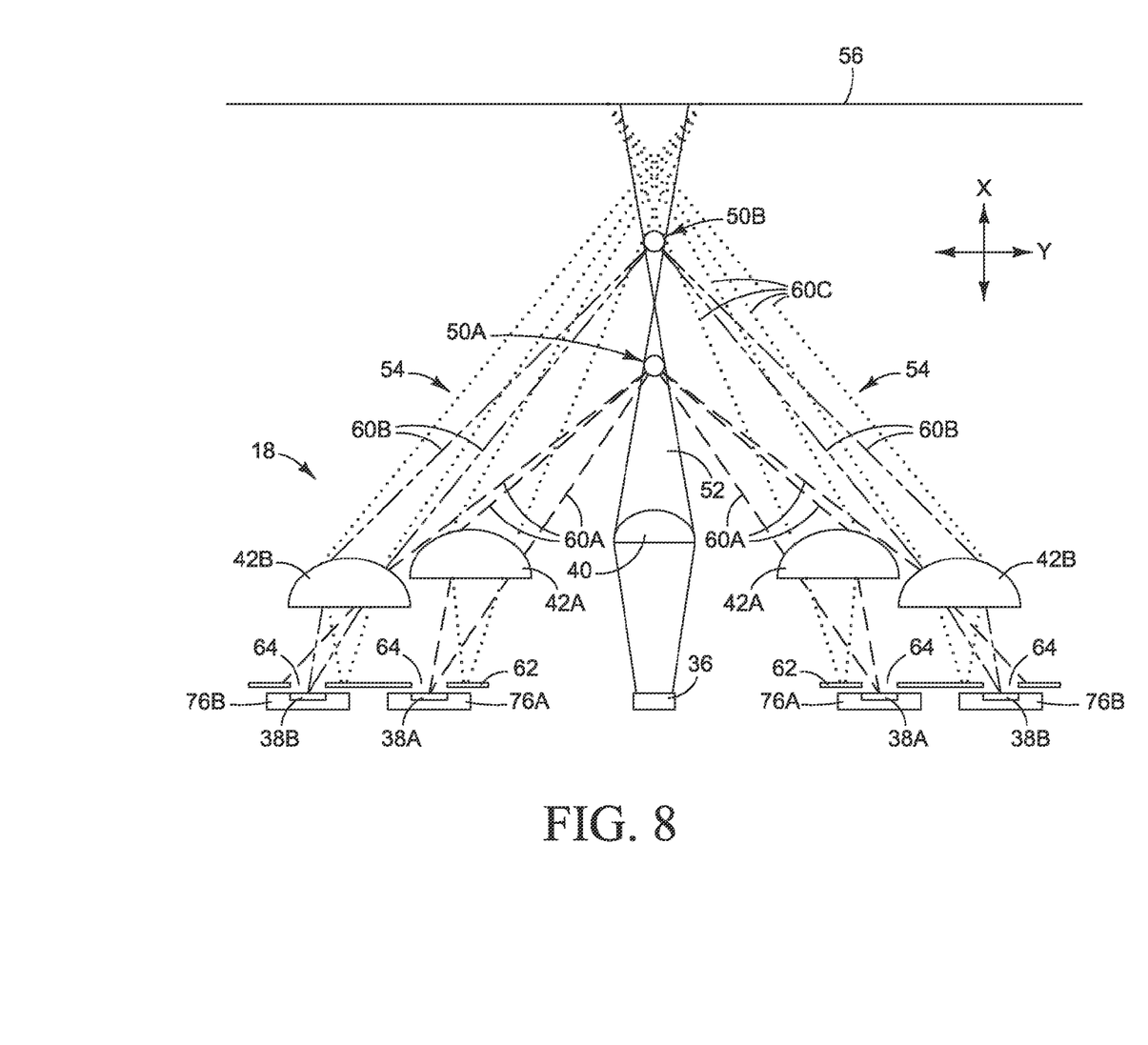
FIG. 8 illustrates a drop detector according to one example of the invention in which an aperture plate is used to help focus the detectors on the desired spaces in the drop zone.

In another example of a drop detector 18 shown in FIG. 8, an aperture plate 62 between each detector 38A, 38B and the corresponding lens 42A, 42B helps block unwanted light from reaching the detector. The size, shape and position of apertures 64 are selected so that plates 62 block light not focused directly on each detector 38A, 38B.

Figure 9:
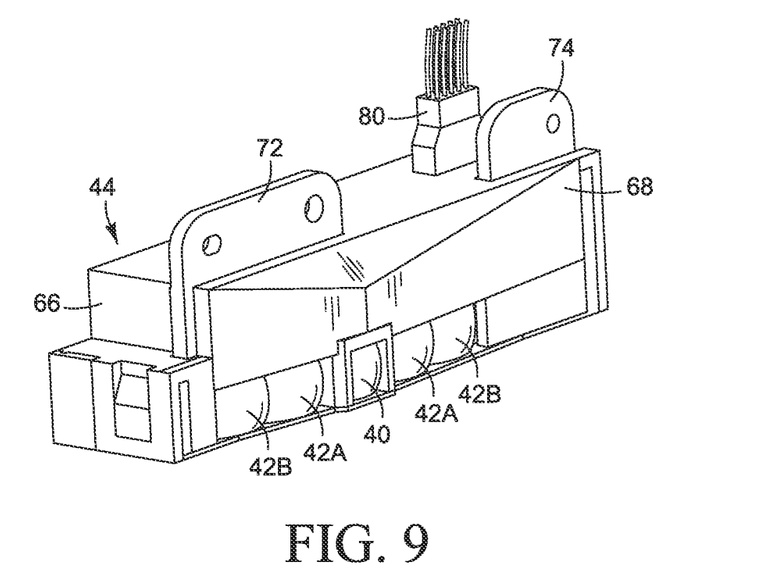
FIGS. 9 and 10 are front side and back side perspective views, respectively, of the exterior of a drop detector module according to one example of the invention.
Figure 10:
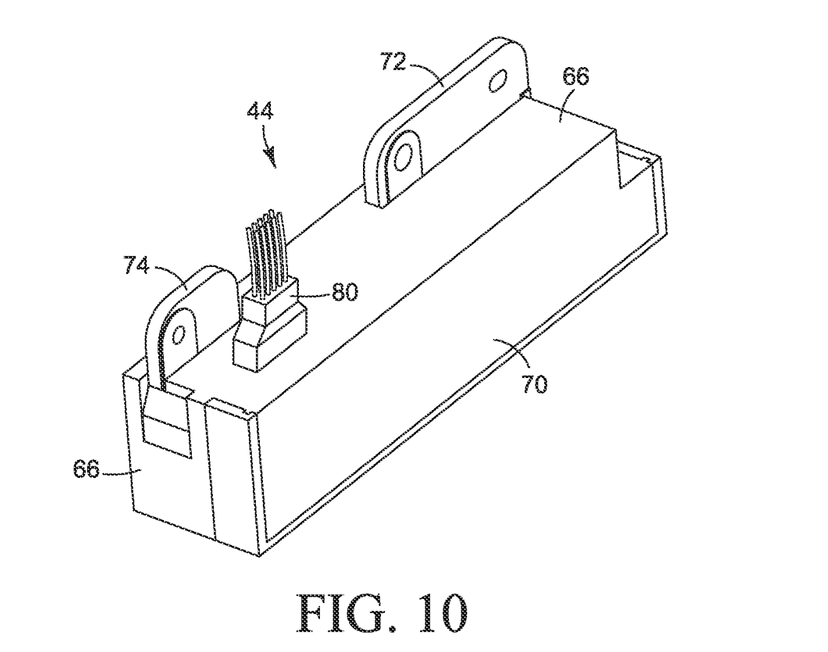

FIGS. 9 and 10 are front side and back side perspective views, respectively, illustrating one example of a new drop detector module 44. FIG. 11 is a perspective view illustrating part of the interior of detector module 44. Referring to FIGS. 9-11, detector module 44 includes a housing 66 and a drop detector 18 supported in housing 66. Housing 66 is constructed as two (or more) separable front and back parts 68 and 70. Flanges 72 and 74 are formed along housing top part 68 for mounting detector module 44 to a carriage 46, as described below with reference to FIGS. 12 and 13.

Drop detector 18 includes a light source 36 and light detector assemblies 76A, 76B containing light detectors 38A, 38B. In addition to a structural base supporting the light detector, each assembly 76A, 76B may also contain amplifier and/or other electronic circuitry for the light detector. Drop detector 18 also includes a lens 40 in front of light source 36 and lenses 42A, 42B in front of light detectors 38A, 38B, respectively. Each detector assembly 76A, 76B is mounted to a printed circuit board (PCB) or a printed circuit assembly (PCA) 78 supported in housing 66. (A PCB with electronic components mounted on the board is commonly referred to as a PCA.) External electrical connections to PCA 78 are made, for example, through any suitable connector 80. As described above with reference to FIG. 4, lens 40 is configured to focus light from light source 36 on to the desired space or spaces in the drop zone; lenses 42A are configured to focus light from one space in the drop zone on inner light detectors 38A; and lenses 42B are configured to focus light from another space in the drop zone on outer light detectors 38B.

Although it is expected that detectors 38A and 38B will usually be aligned in two planes (the X-Y and Y-Z planes in the example shown in FIG. 11), it may be suitable for some drop detector applications to align detectors 38A and 38B in only one plane. Alignment in only the X-Y plane, for example, may still achieve an acceptable degree of modular compaction and sufficient ease of assembly using conventional automated pick and place tooling.

Figure 12:
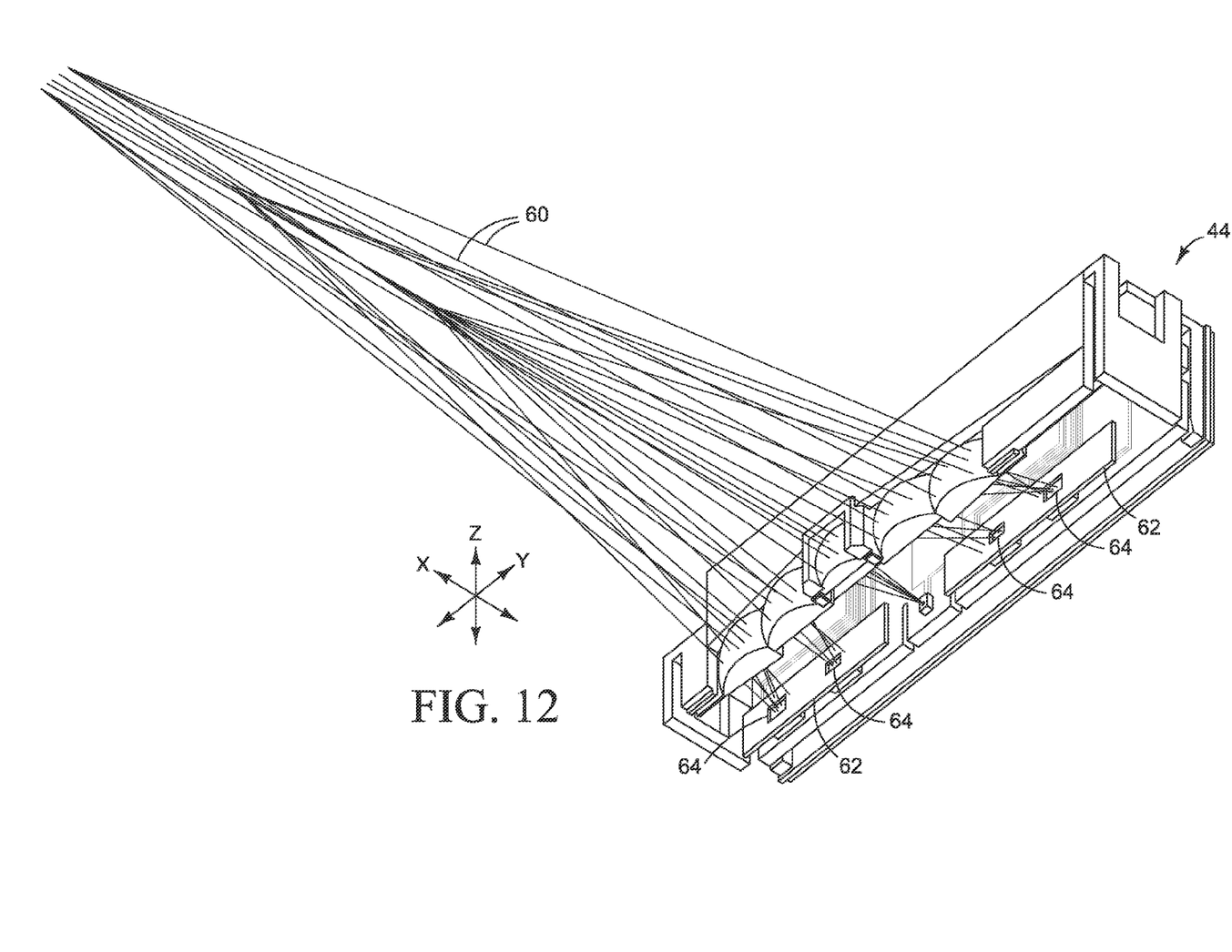
FIG. 12 is a perspective view illustrating part of the interior of the drop detector module of FIGS. 8 and 9 showing another example arrangement of the light detectors in which an aperture plate is used to help focus the detectors on the desired spaces in the drop zone.

FIG. 12 is a perspective view illustrating another example drop detector module 44 that includes an aperture plate 62 with apertures 64 to help focus the detectors on the desired spaces in the drop zone. FIG. 12 also includes lines 60 tracing light rays scattered back toward module 44 to help illustrate the focusing function of lenses 42A, 42B and aperture plate 62.

Figure 13:
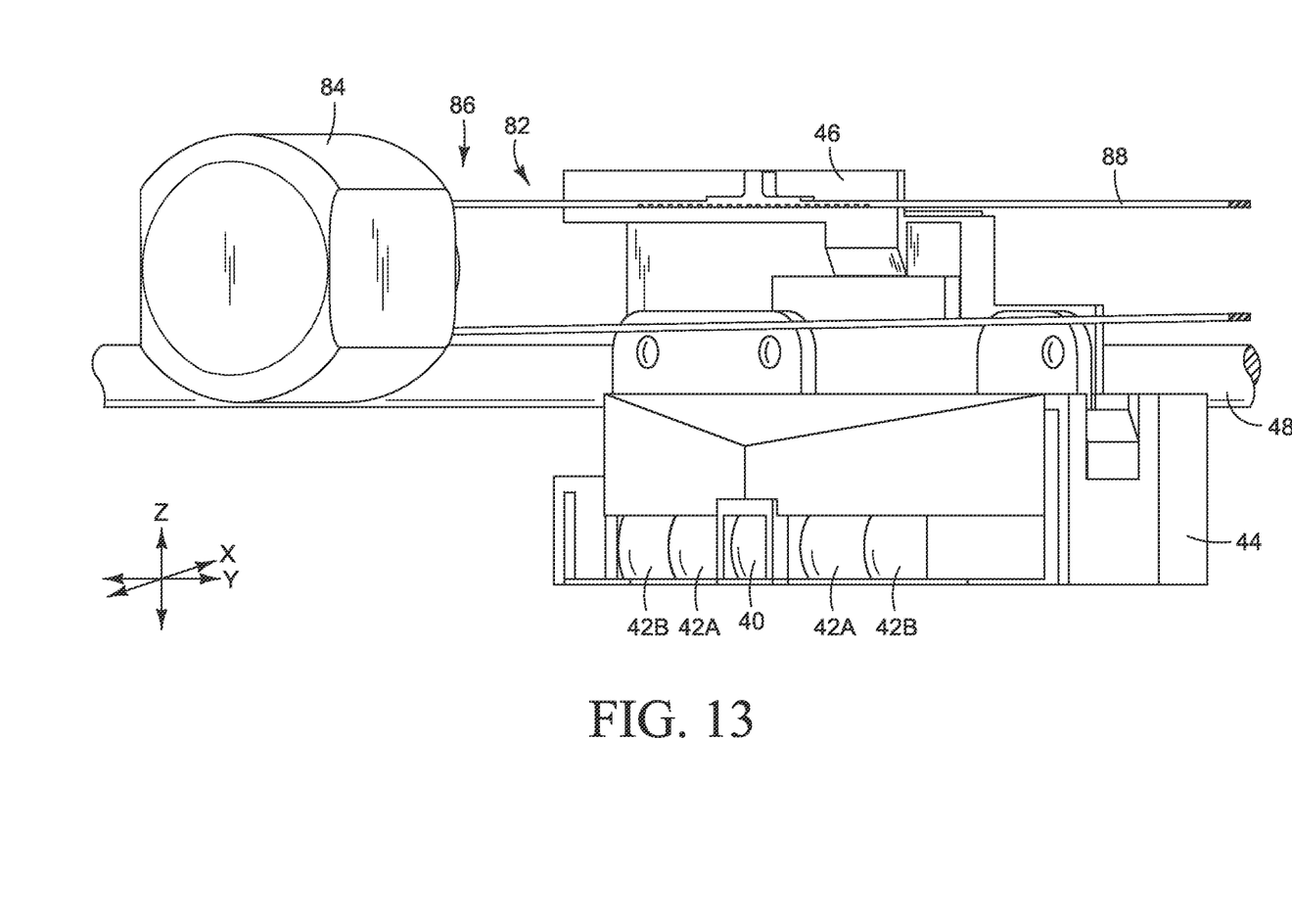
FIGS. 13 and 14 are front side and back side perspective views, respectively, illustrating one example transport assembly for moving a drop detector module along a drop zone.
Figure 14:
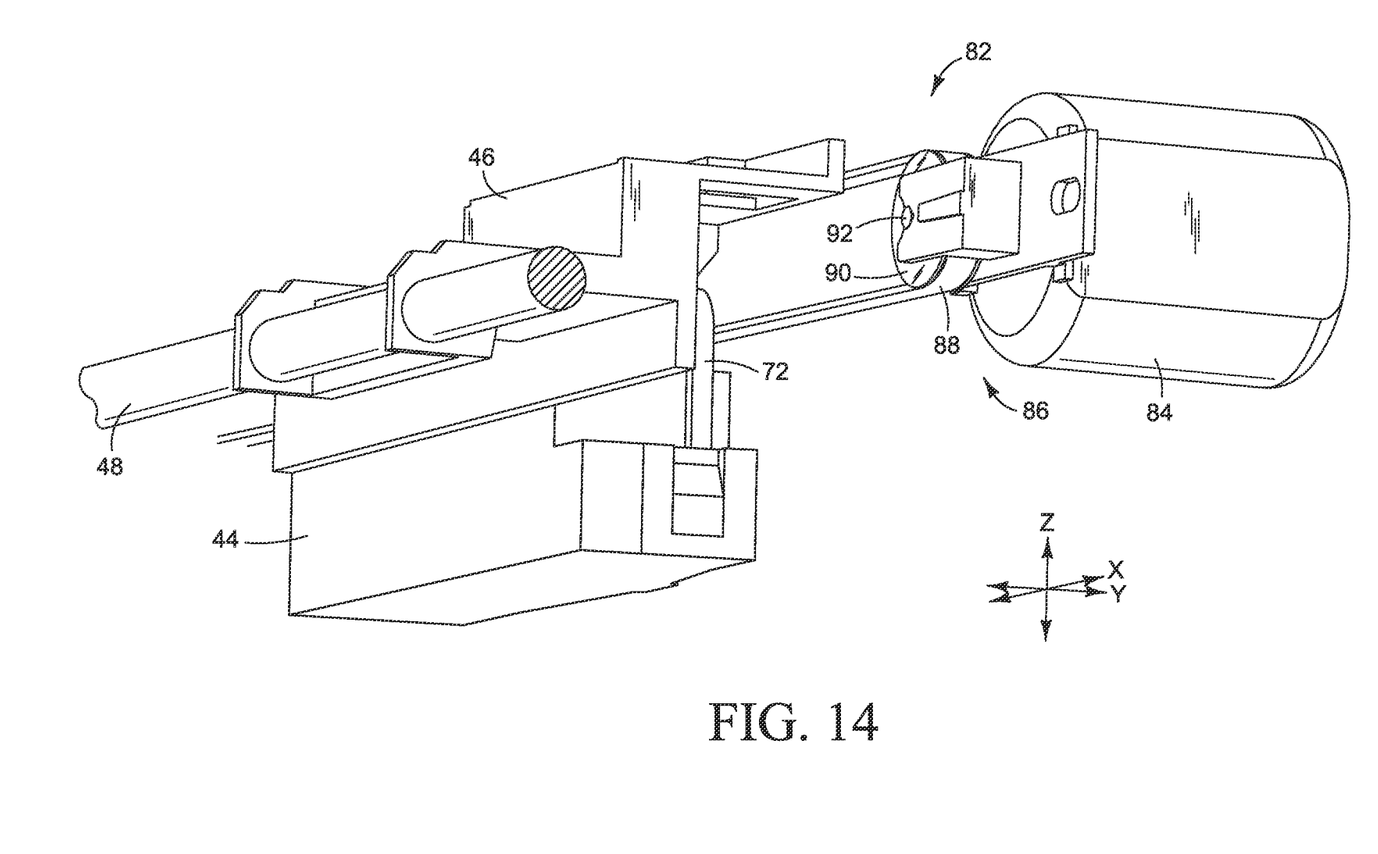

FIGS. 13 and 14 are front side and back side perspective views, respectively, illustrating one example transport assembly 82 for moving a drop detector module 44 along drop zone 26 (FIGS. 2 and 3). Referring to FIGS. 13 and 14, a motor 84 moves carriage 46 carrying detector module 44 along guide rail 48. In the example shown, carriage 46 is operatively connected to motor 84 through a drive train 86 that includes an endless loop belt 88 driven by a pulley 90 attached to a motor drive shaft 92. Referring also to FIG. 2, in one example, carriage 46 is moved to discrete locations along drop zone 26 where light source 36 is energized to project light beam 52 to detect drops 24 at each location. In another example, carriage 46 is scanned along drop zone 26 while light source 36 continuously projects light beam 52 to detect drops 24. A scale and encoder or other suitable position detector may be used to synchronize the movement of carriage 46 with the ejection of drops 24 and to correlate the relative positions of carriage 46 (and thus the position of light source 36 and detectors 38A, 38B) with ink drops 24 as light scattered off drops 24 is detected and the detection signals transmitted to controller 22 (FIG. 1).

As noted at the beginning of this Description, the examples shown in the figures and described above illustrate but do not limit the invention. Other forms, details, and examples may be made and implemented. Therefore, the foregoing description should not be construed to limit the scope of the invention, which is defined in the following claims.

What is claimed is:

1. A drop detector, comprising:
   a light source on a first side of a drop zone for illuminating drops passing through the drop zone with a light beam;
   multiple light detectors on the first side of the drop zone near the light source to detect light scattered off drops passing through the drop zone; and
   multiple lenses each to focus light scattered off drops passing through a space in the drop zone on one of the light detectors.

2. The drop detector of claim 1, wherein each of the light detectors is arranged in the same plane with all of the other light detectors.

3. The drop detector of claim 1, wherein:
   a first one of the multiple lenses to focus light from a first space in the drop zone on a first one of the light detectors; and
   a second one of the lenses to focus light from a second space in the drop zone on a second one of the light detectors.

4. The drop detector of claim 3, wherein:
   the multiple light detectors includes a pair of first light detectors located opposite one another a same first distance from the light source and a pair of second light detectors located opposite one another a same second distance from the light source greater than the first distance; and
   the multiple lenses includes a pair of first lenses each configured to focus light from the first space in the drop zone on a corresponding first light detector and a pair of second lenses each to focus light from the second space in the drop zone on a corresponding second light detector.

5. The drop detector of claim 1, further comprising a carriage coupled to the drop detector.

6. The drop detector of claim 5, wherein the carriage moves in a direction orthogonal to a direction of movement of as print media, and orthogonal to a direction of movement of the drops through the drop zone.

7. The drop detector of claim 1, further comprising a controller to analyze signals representing the light scattered off the drops and detected by the light detectors to determine a number of characteristics of the drops.

8. The drop detector of claim 1, further comprising a non-reflective backplane to restrict scattering of stray light to the detectors.

9. The drop detector of claim 1, wherein the lenses direct unwanted light away from the detectors.

10. The drop detector of claim 1, wherein the space in the drop zone is a first space in the drop zone, and the drop detector further comprising:
    a first lens to focus the light beam of the light source on the first space in the drop zone that corresponds to a first printhead module and a second space in the drop zone that corresponds to a second printhead module.

11. A drop detector module, comprising:
    a housing;
    a light source supported in the housing having a first side and a second side opposite the first side;
    multiple light detectors supported in the housing and arranged in the same plane; and
    multiple lenses supported in the housing, each lens to focus light from a detection space on one of the light detectors, wherein the multiple light detectors comprise a first pair of light detectors comprising a first light detector located on the first side of the light source and a second light detector located on the second side of the light source and the first light detector and the second light detector being positioned a same first distance from the light source.

12. The drop detector module of claim 11, wherein the light detectors arranged in the same plane comprises the light detectors arranged in the same two orthogonal planes.

13. The drop detector module of claim 11, wherein:
a first one of the multiple lenses focuses light from a first detection space corresponding to a first printhead module on a first one of the light detectors; and
a second one of the lenses focuses light from a second detection space corresponding to a second printhead module on a second one of the light detectors.

14. The drop detector module of claim 13, wherein:
the multiple light detectors includes a pair of first light detectors located opposite one another a same first distance from the light source and a pair of second light detectors located opposite one another a same second distance from the light source greater than the first distance; and
the multiple lenses comprise a pair of first lenses each configured to focus light from the first detection space on a corresponding first light detector and a pair of second lenses each configured to focus light from the second detection space on a corresponding second light detector.

15. The drop detector module of claim 11, wherein the multiple light detectors comprise a second pair of light detectors comprising a third light detector located on the first side of the light source and a fourth light detector located on the second side of the light source a same second distance from the light source.

16. The drop detector module of claim 15, wherein the multiple lenses comprise:
a pair of first lenses each located in front of one of the first light detectors, each first lens to focus light from a same first detection space on the corresponding first light detector; and
a pair of second lenses each located in front of one of the second light detectors, each second lens to focus light from a same second detection space on the corresponding second light detector.

17. The drop detector module of claim 15, wherein the second distance from the light source is greater than the first distance.

18. A drop detector module, comprising:
a housing;
a printed circuit board supported in the housing;
a light source mounted to the printed circuit board;
a light source lens supported in the housing in front of the light source to focus a light beam from the light source toward a detection space;
multiple light detectors mounted to the printed circuit board near the light source and arranged in the same plane; and
multiple light detector lenses supported in the housing, each light detector lens positioned in front of a corresponding one of the light detectors to focus light from the detection space on the corresponding light detector,
wherein the multiple light detectors comprise:
a pair of first light detectors located opposite one another a same first distance from the light source; and
a pair of first light detectors located opposite one another a same second distance from the light source greater than the first distance.

19. The drop detector module of claim 18, further comprising an aperture structure supported in the housing between the light detectors and the light detector lenses to block light not focused directly on a light detector.

20. The drop detector module of claim 18, wherein
a first one of the multiple lenses focuses light from a first detection space on a first one of the light detectors; and
a second one of the multiple lenses focuses light from a second detection space on a second one of the light detectors.

* * * * *